(12) United States Patent  (10) Patent No.: US 8,841,299 B2
Hermann et al.  (45) Date of Patent: Sep. 23, 2014

(54) SUBSTITUTED PYRROLO[1,2-A]PYRAZINES AS TANKYRASE INHIBITORS

(71) Applicant: Hoffman-La Roche Inc., South San Francisco, CA (US)

(72) Inventors: Johannes Hermann, Jersey City, NJ (US); Ann Catherine Petersen, Montclair, NJ (US); Jutta Wanner, Montclair, NJ (US); Lin Yi, Basking Ridge, NJ (US)

(73) Assignee: Genentech, Inc., South San Francisco, CA (US)

( * ) Notice: Subject to any disclaimer, the term of this patent is extended or adjusted under 35 U.S.C. 154(b) by 0 days.

(21) Appl. No.: 13/921,942

(22) Filed: Jun. 19, 2013

(65) Prior Publication Data

US 2013/0345226 A1  Dec. 26, 2013

Related U.S. Application Data

(60) Provisional application No. 61/661,913, filed on Jun. 20, 2012.

(51) Int. Cl.
*A61K 31/4985* (2006.01)
*C07D 487/04* (2006.01)

(52) U.S. Cl.
CPC .................................. *C07D 487/04* (2013.01)
USPC .......... 514/249; 544/350; 544/373; 548/335.1

(58) Field of Classification Search
CPC ........................... A61K 31/4985; C07D 487/04
USPC ................. 514/249; 544/350, 373; 548/335.1
See application file for complete search history.

(56) References Cited

FOREIGN PATENT DOCUMENTS

| WO | 2007/138355 A1 | 12/2007 |
|---|---|---|
| WO | 2008/017883 A2 | 2/2008 |
| WO | 2008/017883 A3 | 2/2008 |
| WO | 2008/082887 A2 | 7/2008 |
| WO | 2008/082887 A3 | 7/2008 |
| WO | 2011/130481 A1 | 10/2011 |
| WO | WO 2013/143663 | * 10/2013 |

OTHER PUBLICATIONS

Jordan, V. C. Nature Reviews: Drug Discovery, 2, 2003, 205.*
Hackam, et al. JAMA, 296(14), 2006, 1731-1732.*
Chen et al., "Small molecule-mediated disruption of Wnt-dependent signaling in tissue regeneration and cancer" Nature Chem Biol 5:100-107 (Feb. 2009).
International Search Report and Written Opinion for International Patent Application No. PCT/EP2013/062564.

* cited by examiner

*Primary Examiner* — Douglas M Willis
(74) *Attorney, Agent, or Firm* — Brian L. Buckwalter

(57) ABSTRACT

There are provided compounds of the formula

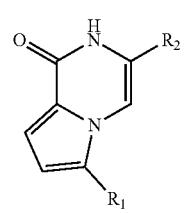

wherein $R_1$ and $R_2$ are as described herein. The compounds are useful as anticancer agents.

7 Claims, No Drawings

SUBSTITUTED PYRROLO[1,2-A]PYRAZINES AS TANKYRASE INHIBITORS

CROSS REFERENCE TO PRIOR APPLICATIONS

The application claims the benefit of priority to U.S. Ser. No. 61/661,913 filed Jun. 20, 2012 the contents of which is incorporated herein by reference in its entirety.

FIELD OF THE INVENTION

The present invention relates to pyrrolopyrazones which act as inhibitors of tankyrase and are useful in the amelioration or treatment of cancer.

BACKGROUND OF THE INVENTION

Cancer is a disease characterized by the loss of appropriate control for cell growth. The American Cancer Society has estimated that there were in excess of 1.5 million new cases of cancer within the United Stated of America in 2010 and approximately 570,000 deaths that year estimated to be attributable to cancer. The World Health Organization has estimated that cancer was the leading cause of death globally in 2010, with the number of deaths caused by cancer growing to 12 million per year by 2030.

It has been suggested that there are 6 capabilities which need to be developed by cells in order to lead to the formation of cancerous lesions. These traits are self-sufficiency in growth signals, insensitivity to anti-growth signals, tissue invasion and metastasis, limitless replication potential, sustained angiogenesis and evasion of apoptosis. Growth signaling is required for cells to transition from a quiescent state into an active proliferative state. These signals are typically transmitted from transmembrane receptors, through signal transduction cascades involving numerous intracellular kinases, eventually resulting in changes in gene expression at the nuclear level within the cell. In recent years there has been much interest in the area of signal transduction inhibitors, particularly kinase inhibitors, and their use for the treatment of cancer. Several examples from this class of compounds have been successfully evaluated in clinical settings and are now commercially available and marketed for the treatment of specific forms of cancer e.g. imatinib tosylate (marketed as Gleevec® by Novartis for the treatment of Philadelphia chromosome-positive chronic myeloid leukemia), lapatinib ditosylate (marketed as Tykerb® by GlaxoSmithKline for the treatment of HER2 positive breast cancer in combination with other chemotherapeutic agents), sunitinib malate (marketed as Sutent® by Pfizer and approved for the treatment of renal cancer) and sorafenib (marketed as Nexavar by Bayer for the treatment of renal cancer).

In addition to the growth factor associated signaling pathways, which predominantly utilize kinase catalyzed transfer of phosphate groups as the key component of the signaling pathway, numerous other signaling pathways also exist within cells and their proper regulation is critical for maintaining correct levels of cell growth and replication. In the emerging area of cancer stem cell inhibition the Wnt, Notch and Hedgehog pathways have received much interest as potential ways in which to avoid tumor relapse and metastasis. The Wnt pathway is instrumental in embryonic development and in tissue maintenance in adults with the activity of individual components within the pathway under tight regulation. In cancer and other diseases cell signaling pathways no longer exhibit the appropriate level of control. In the case of the Wnt pathway, signal transduction is controlled by the relative stabilities of 2 proteins, axin and β-catenin. An overabundance of β-catenin leads to increased Wnt signaling and activation of associated nuclear transcription factors while excess axin results in the degradation of intracellular β-catenin and decreased signaling. Dysregulation of the canonical Wnt signaling pathway has been implicated in a range of human carcinomas such as colon cancer, hepatocellular carcinoma, endometrial ovarian cancer, pilomatricoma skin cancer, prostate cancer, melanoma and Wilms tumor.

In the canonical Wnt signaling pathway signaling is initiated by interaction of a Wnt ligand with a receptor complex containing a Frizzled family member and low-density lipoprotein receptor-related protein. This leads to the formation of a disheveled-frizzled complex and relocation of axin from the destruction complex to the cell membrane. Axin is the concentration limiting component of the destruction complex, and it is this complex which is formed with adenomatous polyposis coli proteins, casein-kinase 1α and glycogen synthase kinase 3β which is responsible for controlling intracellular levels of β-catenin. In the presence of functional destruction complex, β-catenin is sequentially phosphorylated by casein-kinase 1α and glycogen synthase kinase 3β on a conserved set of serine and threonine residues at the amino-terminus. Phosphorylation facilitates binding of β-catenin to β-transducin repeat-containing protein which then mediates ubiquitination and subsequent proteasomal degradation of β-catenin. In the absence of sufficiently elevated concentrations of the destruction complex, un-phosphorylated β-catenin is able to migrate to the cell nucleus and interact with T-cell factor proteins and convert them into potent transcriptional activators through the recruitment of co-activator proteins.

It has recently been reported that intracellular axin levels are influenced by the poly(ADP-ribose) polymerase enzyme family members tankyrase-1 and tankyrase-2 (also known as PARP5a and PARP5b) (*Nature Chemical Biology* 2009, 5, 100 and *Nature* 2009, 461, 614). Tankyrase enzymes are able to poly-ADP ribosylate (PARsylate) axin, which marks this protein for subsequent ubiquitination and proteasomal degradation. Thus, it would be expected that in the presence of an inhibitor of tankyrase catalytic activity, axin protein concentration would be increased, resulting in higher concentration of the destruction complex and decreased concentrations of unphosphorylated intracellular β-catenin and decreased Wnt signaling. An inhibitor of tankyrase-1 and -2 would also be expected to have an effect on other biological functions of the tankyrase proteins e.g. chromosome end protection (telomeres), insulin responsiveness and spindle assembly during mitosis (*Biochimie* 2009, 5, 100).

Therapeutics which are directed at and can correct dysregulation of the Wnt signaling pathway have been implicated in conditions such as bone density defects, coronary disease, late onset Alzheimer's disease, familial exudative vitreoretinopathy, retinal angiogenesis, tetra-amelia, Mullerian-duct regression and virilization, SERKAL syndrome, type 2 diabetes, Fuhrmann syndrome, skeletal dysplasia, focal dermal hypoplasia and neural tube defects. Although the above introduction has focused on the relevance of Wnt signaling in cancer, the Wnt signaling pathway is of fundamental importance and has potential implication in a broad range of human diseases, not necessarily limited to the examples provided above for illustrative purposes.

SUMMARY OF THE INVENTION

One aspect of the invention is a compound of formula I

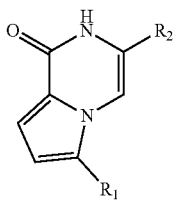

(I)

$R_1$ is selected from the group consisting of $C_{1-6}$ alkyl, halo, cyano, $C_{1-6}$ hydroxyalkyl,

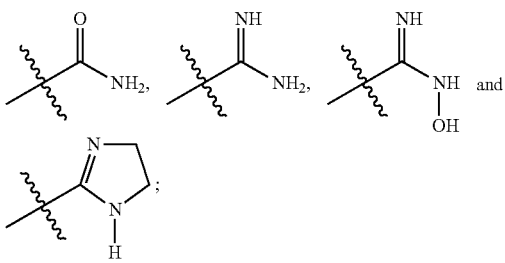

$R_2$ is (i) aryl (ii) heteroaryl said aryl or heteroaryl optionally substituted by one or three groups independently selected from $C_{1-6}$ alkyl, $C_{1-6}$ alkoxy, $C_{1-6}$ haloalkyl or halogen, (iii) piperazinyl or (iv) piperidinyl said piperazinyl or piperidinyl optionally substituted by aryl which is optionally substituted as described above and said heteroaryl is pyridinyl; or, a pharmaceutically acceptable salt thereof.

The present invention also relates to pharmaceutical compositions comprising one or more compounds of the invention, or a pharmaceutically acceptable salt, and a pharmaceutically acceptable carrier or excipient.

The present invention further relates to a method of treating, ameliorating or preventing cancer in a mammal, preferably a human, comprising administering to said mammal a therapeutically effective amount of a compound according to the invention or a pharmaceutically acceptable salt thereof.

DETAILED DESCRIPTION OF THE INVENTION

The phrase "a" or "an" entity as used herein refers to one or more of that entity; for example, a compound refers to one or more compounds or at least one compound. As such, the terms "a" (or "an"), "one or more", and "at least one" can be used interchangeably herein.

The phrase "as defined herein above" refers to the broadest definition for each group as provided in the Summary of the Invention or the broadest claim. In all other embodiments provided below, substituents which can be present in each embodiment and which are not explicitly defined retain the broadest definition provided in the Summary of the Invention.

As used in this specification, whether in a transitional phrase or in the body of the claim, the terms "comprise(s)" and "comprising" are to be interpreted as having an open-ended meaning. That is, the terms are to be interpreted synonymously with the phrases "having at least" or "including at least". When used in the context of a process, the term "comprising" means that the process includes at least the recited steps, but may include additional steps. When used in the context of a compound or composition, the term "comprising" means that the compound or composition includes at least the recited features or components, but may also include additional features or components.

The term "independently" is used herein to indicate that a variable is applied in any one instance without regard to the presence or absence of a variable having that same or a different definition within the same compound. Thus, in a compound in which R" appears twice and is defined as "independently carbon or nitrogen", both R"s can be carbon, both R"s can be nitrogen, or one R" can be carbon and the other nitrogen.

When any variable (e.g., $R^1$, $R^{4a}$, Ar, $X^1$ or Het) occurs more than one time in any moiety or formula depicting and describing compounds employed or claimed in the present invention, its definition on each occurrence is independent of its definition at every other occurrence. Also, combinations of substituents and/or variables are permissible only if such compounds result in stable compounds.

The symbols "*" at the end of a bond or "------" drawn through a bond each refer to the point of attachment of a functional group or other chemical moiety to the rest of the molecule of which it is a part. Thus, for example:

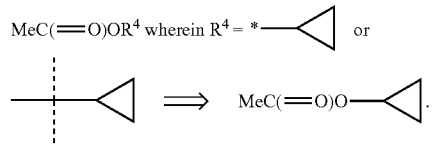

A bond drawn into ring system (as opposed to connected at a distinct vertex) indicates that the bond may be attached to any of the suitable ring atoms.

The term "optional" or "optionally" as used herein means that a subsequently described event or circumstance may, but need not, occur, and that the description includes instances where the event or circumstance occurs and instances in which it does not. For example, "optionally substituted" means that the optionally substituted moiety may incorporate a hydrogen or a substituent.

The term "about" is used herein to mean approximately, in the region of, roughly, or around. When the term "about" is used in conjunction with a numerical range, it modifies that range by extending the boundaries above and below the numerical values set forth. In general, the term "about" is used herein to modify a numerical value above and below the stated value by a variance of 20%.

As used herein, the recitation of a numerical range for a variable is intended to convey that the invention may be practiced with the variable equal to any of the values within that range. Thus, for a variable which is inherently discrete, the variable can be equal to any integer value of the numerical range, including the end-points of the range. Similarly, for a variable which is inherently continuous, the variable can be equal to any real value of the numerical range, including the end-points of the range. As an example, a variable which is described as having values between 0 and 2, can be 0, 1 or 2 for variables which are inherently discrete, and can be 0.0, 0.1, 0.01, 0.001, or any other real value for variables which are inherently continuous.

In one embodiment of the invention there is provided a compound of the formula I wherein $R_1$ and $R_2$ are as defined hereinabove

I

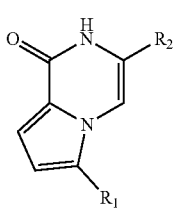

(I)

In another embodiment of the present invention there is provided a compound according to formula I wherein:

$R_1$ is selected from the group consisting of alkyl, halo, cyano, hydroxyalkyl, carboxamide,

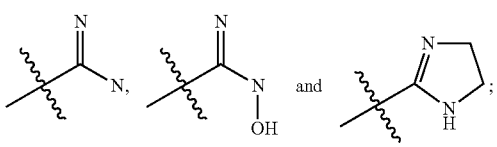

$R_2$ is aryl, substituted aryl, heteroaryl or substituted heteroaryl; or, a pharmaceutically acceptable salt thereof.

In another embodiment of the present invention there is provided a compound according to formula I wherein:

$R_1$ is selected from the group consisting of alkyl, halo, cyano, hydroxyalkyl, carboxamide,

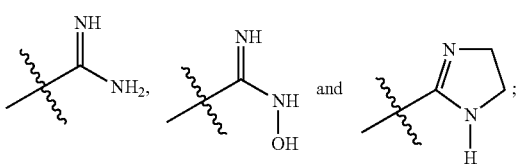

$R_2$ is aryl, substituted aryl, heteroaryl or substituted heteroaryl; or, a pharmaceutically acceptable salt thereof.

In another embodiment of the present invention there is provided a compound according to formula I wherein:

$R_2$ is

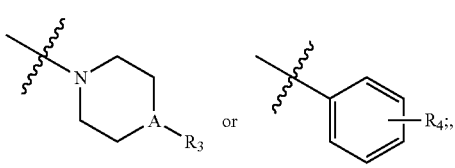

A is CH or N;
$R_3$ is optionally substituted aryl; and,
$R_4$ is trifluoromethyl or methoxy.

In another embodiment of the present invention there is provided a compound according to formula I wherein:

$R_2$ is

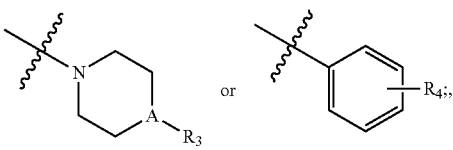

A is C or N,
$R_3$ is aryl or substituted aryl and
$R_4$ is trifluoromethyl or methoxy.

In another embodiment of the present invention there is provided a compound according to formula I wherein $R_2$ is optionally substituted pyridinyl.

In another embodiment of the present invention there is provided a compound of formula I selected from the group consisting of:

6-bromo-3-(4-methoxy-phenyl)-2H-pyrrolo[1,2-a]pyrazin-1-one,
1-oxo-3-(4-trifluoromethyl-phenyl)-1,2-dihydro-pyrrolo[1,2-a]pyrazine-6-carbonitrile,
N-hydroxy-1-oxo-3-(4-trifluoromethyl-phenyl)-1,2-dihydro-pyrrolo[1,2-a]pyrazine-6-carboxamidine,
1-oxo-3-(4-trifluoromethyl-phenyl)-1,2-dihydro-pyrrolo[1,2-a]pyrazine-6-carboxylic acid amide,
1-oxo-3-(4-trifluoromethyl-phenyl)-1,2-dihydro-pyrrolo[1,2-a]pyrazine-6-carboxamidine,
6-(4,5-dihydro-1H-imidazol-2-yl)-3-(4-trifluoromethyl-phenyl)-2H-pyrrolo[1,2-a]pyrazin-1-one,
6-methyl-3-(4-trifluoromethyl-phenyl)-2H-pyrrolo[1,2-a]pyrazin-1-one,
6-hydroxymethyl-3-(4-trifluoromethyl-phenyl)-2H-pyrrolo[1,2-a]pyrazin-1-one,
3-[4-(2-fluoro-phenyl)-piperazin-1-yl]-6-methyl-2H-pyrrolo[1,2-a]pyrazin-1-one and
6-bromo-3-(4-trifluoromethyl-phenyl)-2H-pyrrolo[1,2-a]pyrazin-1-one.

In another embodiment of the present invention there is provided a compound according to formula I wherein $R_1$ and $R_2$ are as defined hereinabove for use in the treatment of cancer.

In another embodiment of the present invention there is provided a compound according to formula I wherein $R_1$ and $R_2$ are as defined hereinabove for the preparation of a medicament for the treatment of cancer.

In another embodiment of the present invention there is provided a pharmaceutical composition containing a compound according to formula I wherein $R_1$ and $R_2$ are as defined hereinabove and at least one pharmaceutically acceptable carrier, diluent or excipient.

In another embodiment of the present invention there is provided a use for a compound according to formula I wherein $R_1$ and $R_2$ are as defined hereinabove and at least one pharmaceutically acceptable carrier, diluent or excipient.

As used herein, the following terms shall have the following definitions.

The term "alkyl" refers to straight- or branched-chain saturated hydrocarbon groups having from 1 to about 12 carbon atoms, including groups having from 1 to about 7 carbon atoms. In certain embodiments, alkyl substituents may be lower alkyl substituents. The term "lower alkyl" refers to alkyl groups having from 1 to 6 carbon atoms, preferably from 1 to 4 carbon atoms. Examples of alkyl groups include, but are not limited to, methyl, ethyl, n-propyl, i-propyl, n-butyl, s-butyl, t-butyl, n-pentyl, and s-pentyl.

The term "alkenyl" as used herein means an unsaturated straight-chain or branched aliphatic hydrocarbon group containing at least one double bond and having 2 to 6, preferably 2 to 4 carbon atoms. Examples of such "alkenyl group" are vinyl, ethenyl, allyl, isopropenyl, 1-propenyl, 2-methyl-1-propenyl, 1-butenyl, 2-butenyl, 3-butenyl, 2-ethyl-1-butenyl, 3-methyl-2-butenyl, 1-pentenyl, 2-pentenyl, 3-pentenyl, 4-pentenyl, 4-methyl-3-pentenyl, 1-hexenyl, 2-hexenyl, 3-hexenyl, 4-hexenyl and 5-hexenyl.

"Alkoxy, alkoxyl or lower alkoxy" refers to any of the above lower alkyl groups which is attached to the remainder of the molecule by an oxygen atom (RO—). Typical lower alkoxy groups include methoxy, ethoxy, isopropoxy or propoxy, butyloxy and the like. Further included within the meaning of alkoxy are multiple alkoxy side chains, e.g. ethoxy ethoxy, methoxy ethoxy, methoxy ethoxy ethoxy and the like and substituted alkoxy side chains, e.g., dimethylamino ethoxy, diethylamino ethoxy, dimethoxy-phosphoryl methoxy and the like.

The term "alkynyl" as used herein means an unsaturated straight-chain or branched aliphatic hydrocarbon group containing one triple bond and having 2 to 6, preferably 2 to 4 carbon atoms. Examples of such "alkynyl group" are ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl and 5-hexynyl.

Amino means the group —$NH_2$.

"Aryl" means a monovalent, monocyclic or bicyclic, aromatic carboxylic hydrocarbon radical, preferably a 6-10 member aromatic ring system. Preferred aryl groups include, but are not limited to, phenyl, naphthyl, tolyl, and xylyl.

Carboxyl or carboxy means the monovalent group —COOH. Carboxy lower alkyl means —COOR, wherein R is lower alkyl. Carboxy lower alkoxy means —COOROH wherein the R is lower alkyl.

Carbonyl means the group RC(=O)R', where R' and R" independently can be any of a number of chemical groups including alkyl.

The term "cycloalkyl" as used herein means any stable monocyclic or polycyclic system which consists of carbon atoms only, any ring of which being saturated, and the term "cycloalkenyl" is intended to refer to any stable monocyclic or polycyclic system which consists of carbon atoms only, with at least one ring thereof being partially unsaturated. Examples of cycloalkyls include, but are not limited to, cyclopropyl, cyclobutyl, cyclopentyl, cyclohexyl, cycloheptyl, adamantyl, cyclooctyl, bicycloalkyls, including bicyclooctanes such as [2.2.2]bicyclooctane or [3.3.0]bicyclooctane, bicyclononanes such as [4.3.0]bicyclononane, and bicyclodecanes such as [4.4.0]bicyclodecane (decalin), or Spiro compounds. Examples of cycloalkenyls include, but are not limited to, cyclopentenyl or cyclohexenyl.

The term "halogen" as used herein means fluorine, chlorine, bromine, or iodine, preferably fluorine and chlorine.

"Heteroaryl" means an aromatic heterocyclic ring system containing up to two rings. Preferred heteroaryl groups include, but are not limited to, thienyl, furyl, indolyl, pyrrolyl, pyridinyl, pyrazinyl, oxazolyl, thiaxolyl, quinolinyl, pyrimidinyl, imidazole substituted or unsubstituted triazolyl and substituted or unsubstituted tetrazolyl.

In the case of aryl or heteroaryl which are bicyclic it should be understood that one ring may be aryl while the other is heteroaryl and both being substituted or unsubstituted.

"Hetero atom" means an atom selected from N, O and S.

"Heterocycle" or "heterocyclic ring" means a substituted or unsubstituted 5 to 8 membered, mono- or bicyclic, non-aromatic hydrocarbon, wherein 1 to 3 carbon atoms are replaced by a hetero atom selected from nitrogen, oxygen or sulfur atom. Examples include pyrrolidin-2-yl; pyrrolidin-3-yl; piperidinyl; morpholin-4-yl and the like which in turn can be substituted.

Hydroxy or hydroxyl is a prefix indicating the presence of a monovalent —O—H group.

"Lower" as in "lower alkenyl" means a group having 1 to 6 carbon atoms.

"Nitro" means —$NO_2$.

Oxo means the group =O.

Pharmaceutically acceptable," such as pharmaceutically acceptable carrier, excipient, etc., means pharmacologically acceptable and substantially non-toxic to the subject to which the particular compound is administered.

"Pharmaceutically acceptable salt" refers to conventional acid-addition salts or base-addition salts that retain the biological effectiveness and properties of the compounds of the present invention and are formed from suitable non-toxic organic or inorganic acids or organic or inorganic bases. Sample acid-addition salts include those derived from inorganic acids such as hydrochloric acid, hydrobromic acid, hydroiodic acid, sulfuric acid, sulfamic acid, phosphoric acid and nitric acid, and those derived from organic acids such as p-toluenesulfonic acid, salicylic acid, methanesulfonic acid, oxalic acid, succinic acid, citric acid, malic acid, lactic acid, fumaric acid, trifluoro acetic acid and the like. Sample base-addition salts include those derived from ammonium, potassium, sodium and, quaternary ammonium hydroxides, such as for example, tetramethylammonium hydroxide. Chemical modification of a pharmaceutical compound (i.e. drug) into a salt is a technique well known to pharmaceutical chemists to obtain improved physical and chemical stability, hygroscopicity, flowability and solubility of compounds. See, e.g., Ansel et al., Pharmaceutical Dosage Forms and Drug Delivery Systems (1995) at pgs. 456-457.

"Substituted," as in substituted alkyl, means that the substitution can occur at one or more positions and, unless otherwise indicated, that the substituents at each substitution site are independently selected from the specified options. The term "optionally substituted" refers to the fact that one or more hydrogen atoms of a chemical group (with one or more hydrogen atoms) can be, but does not necessarily have to be, substituted with another substituent. In the specification where indicated the various groups may be substituted by preferably, 1-3 substituents independently selected from the group consisting of H, carboxyl, amido, hydroxyl, alkoxy, substituted alkoxy, sulfide, sulfone, sulfonamide, sulfoxide, halogen, nitro, amino, substituted amino, lower alkyl, substituted lower alkyl, lower cycloalkyl, substituted lower cycloalkyl, lower alkenyl, substituted lower alkenyl, lower cycloalkenyl, substituted lower cycloalkenyl, aryl, substituted aryl, heteroaryl, substituted heteroaryl, heterocycle or substituted heterocycle.

In general, the nomenclature used in this Application is based on AUTONOM™ v.4.0, a Beilstein Institute computerized system for the generation of IUPAC systematic nomenclature. If there is a discrepancy between a depicted structure and a name given that structure, the depicted structure is to be accorded more weight.

General Reaction Schemes

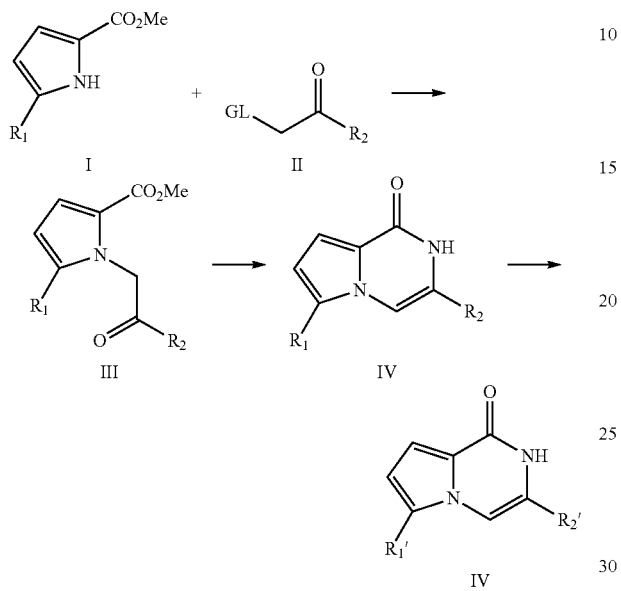

The compound of formula I where $R_1$ is a halide, lower alkyl or nitrile may be commercially available or are able to be prepared by known synthetic methods.

The compound of formula II where $R_2$ is aryl, substituted aryl, heteroaryl or substituted heteroaryl may be commercially available or able to be prepared by known synthetic methods.

The compound of formula III where $R_1$ is halide, lower alkyl or nitrile and $R_2$ is aryl, substituted aryl, heteroaryl or substituted heteroaryl can be prepared from the compound of formula III where $R_1$ is a halide, lower alkyl or nitrile and from the compound of formula II where $R_2$ is aryl, substituted aryl, heteroaryl or substituted heteroaryl through nucleophilic displacement of the leaving group (LG) of the compound of formula II by the pyrrole nitrogen of the compound of formula XI under basic conditions (see for example, Wang, F., Wang, J., Zhang, S., *Molecules* 2004 9:574-582; Temple, D. L., Yevich, J. P., Covington, R. R., Hanning, C. A., Seidehamel, R. J., Mackey, H. K., Bartek, M. J., *J. Med. Chem.* 1979 22(5):505-510).

The compound of formula IV where $R_1$ is halide, lower alkyl, or nitrile and where $R_2$ is aryl, substituted aryl, heteroaryl or substituted heteroaryl can be prepared from the compound of formula III where $R_1$ is halide, lower alkyl or nitrile and where $R_2$ is aryl, substituted aryl, heteroaryl or substituted heteroaryl through cyclization followed by treatment with an ammonia equivalent (see e.g., Temple, D. L., Yevich, J. P., Covington, R. R., Hanning, C. A., Seidehamel, R. J., Mackey, H. K., Bartek, M. J., *J. Med. Chem.* 1979 22(5):505-510; Butler, R. N., Gavin, H. A., Cunningham, D., McArdle, P., *J. Chem. Soc. Perkin Trans. I* 1993 883-884).

The compound of formula V where $R_1$ is halide, lower alkyl or nitrile and where $R_2$ is aryl, substituted aryl, heteroaryl or substituted heteroaryl can be prepared from the compound of formula IV where $R_1$ is halide, lower alkyl or nitrile and where $R_2$ is aryl, substituted aryl, heteroaryl or substituted heteroaryl where $R_1$ and/or $R_2$ embody functional groups that can further be elaborated through standard chemical manipulation to the compound of formula V where $R_1$ and/or $R_2$ are $R_1'$ and/or $R_2'$ (see for example, Lange, U. E. W., Baucke, D., Hornberger, W., Mack, H., Seitz, W., Hoffken, H. W., *Bioorg. Med. Chem. Lett.* 2003 13(12):2029-2033; Chapleo, C. B., Fagen, G. P., WO1992006972 A1; Beigelman, L., Buckman, B., Wang, G., Matulic-Adamic, J., Stoycheva, A. D., Andrews, S. W., Misialek, S. M., Rajagopalin, P. T., Fryer, A. M., Gunawardana, I., Haas, J., Huang, L., Madduru, M. R., Zhang, G., Kossen, K., Serebryany, V., WO 2008/100867 A2).

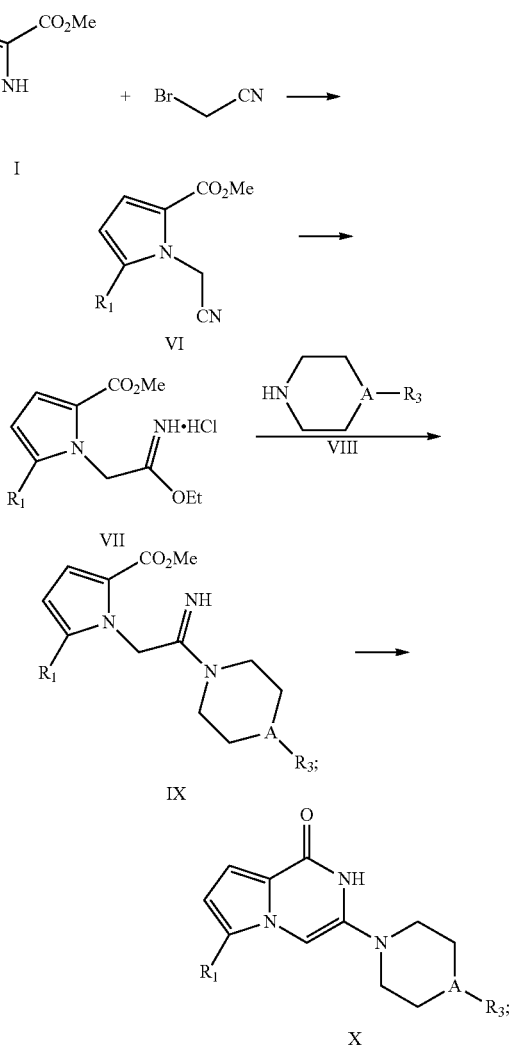

A = N, C or C—$R_4$

The compound of formula I where $R_1$ is halide, lower alkyl or nitrile may be commercially available or able to be prepared by known synthetic methods.

The compound of formula VI where $R_1$ is halide, lower alkyl or nitrile can be prepared by treating the compound of formula I where $R_1$ is halide, lower alkyl, nitrile with bromoacetonitrile under basic conditions (see for example, Roy, S., Eastment, A., Gribble, G. W., *Tetrahedron* 2006 62:7838-7845).

The compound of formula VII where $R_1$ is halide, lower alkyl or nitrile can be prepared by treating the compound of formula VI where $R_1$ is halide, lower alkyl or nitrile under acidic conditions in the presence of an alcohol to form the appropriate imidate ester (see e.g., McElvain, S. M., Stevens, C. L., *J. Amer. Chem. Soc.* 1946, 68:1917-1921).

The compound of formula VIII where $R_3$ is aryl, substituted aryl, heteroaryl or substituted heteroaryl and A is nitrogen, carbon or a substituted carbon (C—$R_4$; where $R_4$ is lower alkyl, hydroxyl or nitrile) may be commercially available or able to be prepared by standard synthetic methods.

The compound of formula IX where $R_1$ is halide, lower alkyl or nitrile and where $R_3$ is aryl, substituted aryl, heteroaryl or substituted heteroaryl and A is nitrogen, carbon or a substituted carbon (C—$R_4$; where $R_4$ is lower alkyl, hydroxyl or nitrile) can be prepared from compound of formula VII where $R_1$ is halide, lower alkyl or nitrile and from the compound of formula VIII where $R_3$ is nitrogen, carbon or a substituted carbon (C—$R_4$; where $R_4$ is lower alkyl, hydroxyl or nitrile) by heating them together (see for example, McCarthy, J. R., Wright, D. L., Schuster, A. J., Abdallah, A. H., Shea, P. J., Eyster, R., *J. Med. Chem.* 1985 28:1721-1727).

The compound of formula X where $R_1$ is halide, lower alkyl or nitrile and where $R_3$ is aryl, substituted aryl, heteroaryl or substituted heteroaryl and A is nitrogen, carbon or a substituted carbon (C—$R_4$; where $R_4$ is lower alkyl, hydroxyl or nitrile) can be prepared from the compound of formula IX where $R_1$ is halide, lower alkyl or nitrile and where $R_3$ is nitrogen, carbon or a substituted carbon (C—$R_4$; where $R_4$ is lower alkyl, hydroxyl or nitrile) by heating under basic conditions to affect a ring cyclization (thermally or in a microwave) (see for example, Sakamoto, T., Kondo, Y., Yamanaka, H., *Chem. Pharm. Bull.* 1985 33(11):4764-4768).

The following preparations and examples are given to enable those skilled in the art to more clearly understand and to practice the present invention. They should not be considered as limiting the scope of the invention, but merely as being illustrative and representative thereof.

Abbreviations $Ac_2O$ Acetic anhydride
AcOH Acetic acid
DBU 1,8-Diazabicyclo[5.4.0]undec-7-ene
DCE 1,2-Dichloroethane
DCM Dichloromethane/Methylene chloride
DIPEA Diisopropylethylamine
DMF N,N-dimethylformamide
DMSO Dimethyl sulfoxide
EDCI 1-(3-Dimethylaminopropyl)-3-ethylcarbodiimide hydrochloride
$Et_2O$ Diethyl ether
EtOH Ethanol/Ethyl alcohol
EtOAc Ethyl acetate
IWR2 4-((1S,2R,6S,7R)-3,5-Dioxo-4-aza-tricyclo[5.2.1.0*2,6]dec-8-en-4-yl)-N-(4-methyl-quinolin-8-yl)-benzamide
HOBt 1-Hydroxybenzotriazole
LDA Lithium diisopropylamide
LiHMDS Lithium bis(trimethylsilyl)amide
m-CPBA 3-Chloroperoxybenzoic acid
MeOH Methanol/Methyl alcohol
MW Microwaves
NMP 1-Methyl-2-pyrrolidinone
PMB 4-Methoxy benzyl
RT Room temperature
TBME tert-Butyl methyl ether
TFA Trifluoroacetic acid
$Tf_2O$ Trifluoromethanesulfonic anhydride
THF Tetrahydrofuran
TLC Thin layer chromatography
TNKS Tankyrase
Tris 2-amino-2-hydroxymethyl-propane-1,3-diol
XAV939 2-(4-Trifluoromethyl-phenyl)-3,5,7,8-tetrahydro-thiopyrano[4,3-d]pyrimidin-4-one General Conditions Compounds of the invention can be made by a variety of methods depicted in the illustrative synthetic reactions described below in the Examples section.

The starting materials and reagents used in preparing these compounds generally are either available from commercial suppliers, such as Aldrich Chemical Co., or are prepared by methods known to those skilled in the art following procedures set forth in references such as Fieser and Fieser's *Reagents for Organic Synthesis*; Wiley & Sons: New York, 1991, Volumes 1-15; Rodd's *Chemistry of Carbon Compounds*, Elsevier Science Publishers, 1989, Volumes 1-5 and Supplementals; and *Organic Reactions*, Wiley & Sons: New York, 1991, Volumes 1-40. It should be appreciated that the synthetic reaction schemes shown in the Examples section are merely illustrative of some methods by which the compounds of the invention can be synthesized, and various modifications to these synthetic reaction schemes can be made and will be suggested to one skilled in the art having referred to the disclosure contained in this application.

The starting materials and the intermediates of the synthetic reaction schemes can be isolated and purified if desired using conventional techniques, including but not limited to, filtration, distillation, crystallization, chromatography, and the like. Such materials can be characterized using conventional means, including physical constants and spectral data.

Unless specified to the contrary, the reactions described herein are typically conducted under an inert atmosphere at atmospheric pressure at a reaction temperature range of from about −78° C. to about 150° C., often from about 0° C. to about 125° C., and more often and conveniently at about room (or ambient) temperature, e.g., about 20° C.

Preparative reverse-phase high-pressure liquid chromatography (RP HPLC) was performed using one of the following systems: (A). a Waters Delta prep 4000 pump/controller, a 486 detector set at 215 nm, and a LKB Ultrorac fraction collector; or (B). a Sciex LC/MS system with a 150 EX single quad mass spec, a Shimadzu LC system, a LEAP autoinjector, and a Gilson fraction collector. The sample was dissolved in a mixture of acetonitrile/20 mM aqueous ammonium acetate or acetonitrile/water/TFA, applied on a Pursuit C-18 20×100 mm column and eluted at 20 mL/min with a linear gradient of 10%-90% B, where (A): 20 mM aqueous ammonium acetate (pH 7.0) and (B): acetonitrile or (A): water with 0.05% TFA and (B): acetonitrile with 0.05% TFA.

Flash chromatography was performed using standard silica gel chromatography, pre-packed silica columns (Analogix) with an Analogix BSR pump system or AnaLogix IntelliFlash Automated systems. Reactions heated in a microwave were performed using the Biotage Initiator 60 microwave or the CEM Explore microwave

EXAMPLE 1

6-Bromo-3-(4-methoxy-phenyl)-2H-pyrrolo[1,2-a]pyrazin-1-one

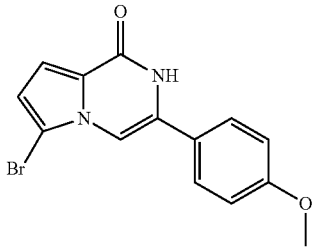 [SMILES: COc1ccc(-c2cn3c(Br)ccc3c(=O)[nH]2)cc1]

A mixture of ethyl 5-bromo-1H-pyrrole-2-carboxylate (0.13 g, 0.64 mmol), 2-bromo-1-(4-methoxyphenyl)ethanone (160 mg, 0.69 mmol) and potassium carbonate (132 mg, 0.95 mmol) in N,N-dimethylformamide (4 mL) was stirred at room temperature overnight. At this time, the light brown reaction mixture was quenched with water. The resulting precipitate was collected by filtration and dried in vacuo. The resulting solid was dissolved in methylene chloride, concentrated in vacuo and then triturated with diethyl ether. The resulting solid was collected by filtration and dried in vacuo to afford 5-bromo-1-[2-(4-methoxy-phenyl)-2-oxo-ethyl]-1H-pyrrole-2-carboxylic acid methyl ester (155 mg, 69%) as light brown solid. $^1$H NMR (chloroform-d) δ ppm 8.00 (d, J=8.8 Hz, 2H), 6.96-7.07 (m, 3H), 6.85 (d, J=1.8 Hz, 1H), 5.71 (s, 2H), 3.91 (s, 3H), 3.75 (s, 3H).

A mixture of 5-bromo-1-[2-(4-methoxy-phenyl)-2-oxo-ethyl]-1H-pyrrole-2-carboxylic acid methyl ester (0.15 g, 0.43 mmol) and ammonium acetate (170 mg, 2.21 mmol) in glacial acetic acid (2 mL) was heated at 130° C. overnight. The reaction was stopped, and the recovered starting material was suspended in 1,4-dioxane (2 mL), treated with ammonium acetate (170 mg, 2.21 mmol) and then was heated in a sealed tube at 120° C. for 5 h. At this time, the reaction was treated with additional ammonium acetate, and the mixture continued stirring at 120° C. overnight. At this time, the reaction was treated with water. The resulting precipitate was collected by filtration, washed with water (2×) and dried in vacuo to afford 6-bromo-3-(4-methoxy-phenyl)-2H-pyrrolo[1,2-a]pyrazin-1-one (78 mg, 55%) as red solid. $^1$H NMR (DMSO-d$_6$) δ ppm 7.54-7.63 (m, 4H), 7.03 (d, J=9.0 Hz, 2H), 6.96 (d, J=1.3 Hz, 1H), 3.80 (s, 3H). LC-MS calcd. for $C_{14}H_{12}BrN_2O_2$ [(M+H)$^+$] 319, obsd. 319.0.

EXAMPLE 2

1-Oxo-3-(4-trifluoromethyl-phenyl)-1,2-dihydro-pyrrolo[1,2-a]pyrazine-6-carbonitrile

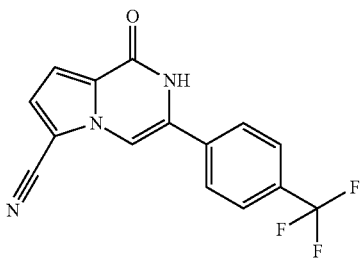 [SMILES: N#Cc1ccc2c(=O)[nH]c(-c3ccc(C(F)(F)F)cc3)cn12]

A mixture of 6-bromo-3-(4-(trifluoromethyl-phenyl)-2H-pyrrolo[1,2-a]pyrazin-1-one (Example 128) (0.105 g, 0.29 mmol), zinc cyanide (21.0 mg, 0.18 mmol) and 2-dicyclohexylphosphino-2',4',6'-triisopropylbiphenyl (14.0 mg, 29.4 μmol) was suspended in N,N-dimethylformamide (1.5 mL) under argon. The reaction was then treated with tris(dibenzylideneacetone)dipalladium(0) (13.5 mg, 14.7 μmol). Argon was bubbled through the reaction mixture for 5 min. The mixture was then heated at 100° C. in a sealed vial for 24 h. At this time, the reaction mixture was transferred to a microwave vial (solid residues stayed behind). The reaction was then treated with zinc cyanide (21.0 mg, 0.18 mmol), 2-dicyclohexylphosphino-2',4',6'-triisopropylbiphenyl (14.0 mg, 29.4 μmol) and tris(dibenzylideneacetone)dipalladium(0) (13.5 mg, 14.7 μmol). The reaction mixture was stirred and heated at 130° C. in a microwave for 1 h. At this time, the mixture was filtered through Celite®. The filtrate was diluted with water (5 mL). The resulting precipitate was collected by filtration and dried in vacuo. Flash chromatography (12 g silica column, 3-40% ethyl acetate/hexanes) afforded 1-oxo-3-(4-trifluoromethyl-phenyl)-1,2-dihydro-pyrrolo[1,2-a]pyrazine-6-carbonitrile (63 mg, 69%) as yellow solid. $^1$H NMR (methanol-d$_4$) δ ppm 8.02 (d, J=1.5 Hz, 9H), 7.80-7.90 (m, 4H), 7.74 (s, 1H), 7.41 (d, J=0.8 Hz, 1H). LC-MS calcd. for $C_{15}H_7F_3N_3O$ [(M−H)$^−$] 302, obsd. 302.0.

EXAMPLE 3

N-Hydroxy-1-oxo-3-(4-trifluoromethyl-phenyl)-1,2-dihydro-pyrrolo[1,2-a]pyrazine-6-carboxamidine

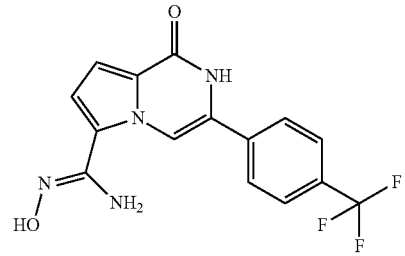 [SMILES: N/C(=N\O)c1ccc2c(=O)[nH]c(-c3ccc(C(F)(F)F)cc3)cn12]

A mixture of 1-oxo-3-(4-trifluoromethyl-phenyl)-1,2-dihydro-pyrrolo[1,2-a]pyrazine-6-carbonitrile (Example 2), (0.05 g, 0.16 mmol), hydroxylamine hydrochloride (15 mg, 0.22 mmol) and N,N-diisopropylethylamine (86.4 μL, 0.49 mmol,) was stirred in methylene chloride (0.5 mL), methanol (0.5 mL) and N,N-dimethylformamide (0.2 mL) at 45° C. for 2 d. At this time, the resulting solids were collected by filtration to afford N-hydroxy-1-oxo-3-(4-trifluoromethyl-phenyl)-1,2-dihydro-pyrrolo[1,2-a]pyrazine-6-carboxamidine (40 mg, 70%) as an off-white solid. $^1$H NMR (methanol-d$_4$) δ ppm 7.83 (q, J=8.4 Hz, 4H), 7.73 (s, 2H), 7.37 (s, 1H). LC-MS calcd. for $C_{15}H_{12}F_3N_4O_2$ [(M+H)$^+$] 337, obsd. 337.0.

EXAMPLE 4

1-Oxo-3-(4-trifluoromethyl-phenyl)-1,2-dihydro-pyrrolo[1,2-a]pyrazine-6-carboxylic acid amide

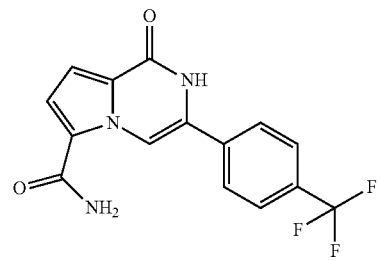 [SMILES: NC(=O)c1ccc2c(=O)[nH]c(-c3ccc(C(F)(F)F)cc3)cn12]

A mixture of 1-oxo-3-(4-trifluoromethyl-phenyl)-1,2-di-hydro-pyrrolo[1,2-a]pyrazine-6-carbonitrile, (Example 2), (0.03 g, 98.9 82 mol), suspended in tetrahydrofuran (1 mL) was treated with a solution of lithium hydroxide (7.11 mg, 0.29 mmol) in water (500 μL) and 30 wt % aqueous hydrogen peroxide (40.4 μL, 0.39 mmol). The reaction was stirred at room temperature overnight. At this time, the reaction was concentrated in vacuo. The resulting residue was triturated with water. The resulting solid was collected by filtration and then dried in vacuo to afford 1-oxo-3-(4-trifluoromethyl-phenyl)-1,2-dihydro-pyrrolo[1,2-a]pyrazine-6-carboxylic acid amide (20 mg, 61%) as light yellow solid. $^1$H NMR (methanol-$d_4$) δ ppm 7.94 (d, J=1.5 Hz, 1H), 7.85-7.90 (m, 2H), 7.80-7.84 (m, 2H), 7.77 (s, 1H), 7.52 (d, J=0.8 Hz, 1H). LC-MS calcd. for $C_{15}H_{11}F_3N_3O_2$ [(M+H)$^+$] 322, obsd. 322.0.

EXAMPLE 5

1-Oxo-3-(4-trifluoromethyl-phenyl)-1,2-dihydro-pyrrolo[1,2-a]pyrazine-6-carboxamidine

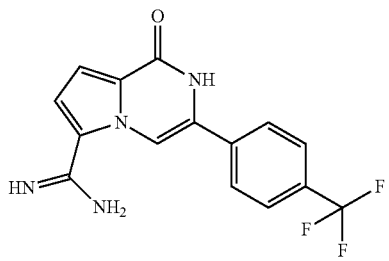 [SMILES: N=C(N)c1ccc2c(=O)[nH]c(-c3ccc(C(F)(F)F)cc3)cn12]

A mixture of N-hydroxy-1-oxo-3-(4-trifluoromethyl-phenyl)-1,2-dihydro-pyrrolo[1,2-a]pyrazine-6-carboxamidine (Example 3) (0.03 g, 89.2 μmol) suspended in methanol (1.5 mL) and glacial acetic acid (0.15 mL) was treated with 10% palladium on carbon (5 mg). The reaction was stirred at room temperature under hydrogen (1 atm) at 50° C. for 2 h. The reaction was treated with ammonium formate (16.9 mg, 0.27 mmol) and then heated at reflux for 5 h. The reaction mixture was treated with slurry of Raney nickel in water (~0.2 mL). The resulting mixture was stirred under hydrogen (1 atm) at room temperature overnight. At this time the reaction was filtered through Celite®. The filtrate was concentrated in vacuo to afford a light yellow semi-solid. The solid was triturated with diethyl ether, collected by filtration and then dried in vacuo to afford a light green solid. This solid was further triturated with a saturated aqueous sodium bicarbonate solution, collected by filtration and dried in vacuo to afford 1-oxo-3-(4-trifluoromethyl-phenyl)-1,2-dihydro-pyrrolo[1,2-a]pyrazine-6-carboxamidine (13 mg, 44%) as light brown solid. $^1$H NMR (methanol-$d_4$) δ ppm 8.11 (s, 1H), 7.92 (d, J=8.8 Hz, 2H), 7.78-7.84 (m, 3H), 7.50-7.56 (m, 1H). LC-MS calcd. for $C_{15}H_{11}F_3N_4O$ [(M+H)$^+$] 321, obsd. 321.0.

EXAMPLE 6

6-(4,5-Dihydro-1H-imidazol-2-yl)-3-(4-trifluoromethyl-phenyl)-2H-pyrrolo[1,2-a]pyrazin-1-one

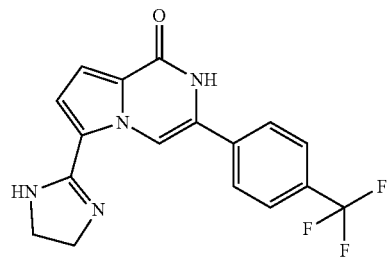 [SMILES: O=c1[nH]c(-c2ccc(C(F)(F)F)cc2)cn2c(C3=NCCN3)ccc12]

A mixture of 1-oxo-3-(4-trifluoromethyl-phenyl)-1,2-dihydro-pyrrolo[1,2-a]pyrazine-6-carbonitrile (Example 2) (0.03 g, 98.9 μmol), phosphorus pentasulfide (8 mg, 36.0 μmol) and ethane-1,2-diamine (0.5 mL, 7.48 mmol) in a sealed vial was heated at 120° C. for 2 h. At this time, the green/yellow reaction mixture was allowed to cool to room temperature and was then poured onto ice water. The resulting solid was collected by filtration, washed with water and dried in vacuo to afford 6-(4,5-dihydro-1H-imidazol-2-yl)-3-(4-trifluoromethyl-phenyl)-2H-pyrrolo[1,2-a]pyrazin-1-one (28 mg, 81%) as light yellow solid. $^1$H NMR (methanol-$d_4$) δ ppm 7.86-7.91 (m, 3H), 7.77-7.84 (m, 3H), 7.44 (d, J=0.8 Hz, 1H), 3.81 (s, 4H). LC-MS calcd. for $C_{17}H_{14}F_3N_4O$ [(M+H)$^+$] 347, obsd. 347.0.

EXAMPLE 7

6-Methyl-3-(4-trifluoromethyl-phenyl)-2H-pyrrolo[1,2-a]pyrazin-1-one

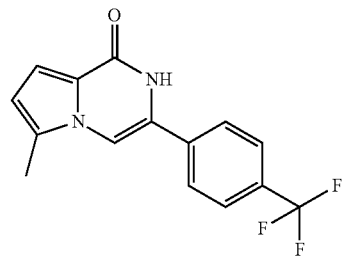 [SMILES: Cc1ccc2c(=O)[nH]c(-c3ccc(C(F)(F)F)cc3)cn12]

A mixture of 6-bromo-3-(4-trifluoromethyl-phenyl)-2H-pyrrolo[1,2-a]pyrazin-1-one (Example 128) (0.1 g, 0.28 mmol), 1,1'-bis(diphenylphosphino)ferrocenedichloro palladium(II) dichloromethane complex (61.5 mg, 84.0 μmol) and N,N-dimethylethanolamine (14.1 μL, 140 μmol) in tetrahydrofuran (1.5 mL) under argon was treated with 1.2M dimethylzinc in toluene (280 μL, 0.33 mmol). The reaction mixture was stirred in a sealed vial at 50° C. overnight. At this time, the reaction was treated with additional dimethylzinc (0.14 mL). The reaction mixture was stirred at 50° C. over the weekend. At this time, the reaction mixture was cooled to room temperature, quenched with a saturated aqueous ammonium chloride solution and then extracted with ethyl acetate. Methanol (0.5 mL) was added, the mixture was filtered and the layers were separated. The organic layers were absorbed onto silica gel. Flash chromatography (12 g silica column, 0-40% ethyl acetate/hexanes) followed by trituration with methylene chloride afforded 6-methyl-3-(4-trifluoromethyl-phenyl)-2H-pyrrolo[1,2-a]pyrazin-1-one (14 mg, 17%) as white solid. $^1$H NMR (methanol-d$_4$) δ ppm 7.76-7.86 (m, 4H), 7.69 (s, 1H), 7.28 (s, 1H), 6.95, (s, 1H), 2.28 (s, 3H). LC-MS calcd. for C$_{15}$H$_{12}$F$_3$N$_2$O [(M+H)$^+$] 293, obsd. 293.1.

EXAMPLE 8

6-Hydroxymethyl-3-(4-trifluoromethyl-phenyl)-2H-pyrrolo[1,2-a]pyrazin-1-one

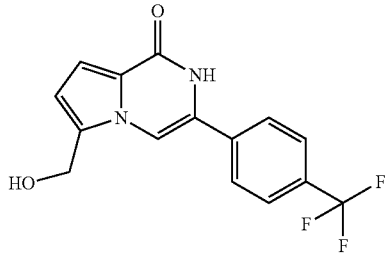 [SMILES: O=c1[nH]c(-c2ccc(C(F)(F)F)cc2)cn2c(CO)ccc12]

A mixture of 1-oxo-3-(4-trifluoromethyl-phenyl)-1,2-dihydro-pyrrolo[1,2-a]pyrazine-6-carbonitrile (Example 2) (55 mg, 0.18 mmol) in methylene chloride (1 mL) cooled –75° C. was treated dropwise with 1M diisobutylaluminum hydride in methylene chloride (275 µL, 0.27 mmol). The reaction was stirred at –75° C. for 1.5 h. At this time, the reaction was treated with additional 1M diisobutylaluminum hydride in methylene chloride (0.1 mL, 0.1 mmol) and allowed to stir at –75° C. for an additional 1 h. At this time, the reaction was treated with a solution of Rochelle's salt, and the mixture was allowed to warm up to room temperature where it stirred overnight. At this time, the resulting suspension was absorbed onto silica gel. Flash chromatography (4 g silica column, 0-50% ethyl acetate/hexanes) afforded 1-oxo-3-(4-trifluoromethyl-phenyl)-1,2-dihydro-pyrrolo[1,2-a]pyrazine-6-carbaldehyde (22 mg, 40%) as light yellow solid. $^1$H NMR (acetone-d$_6$) δ ppm 10.02 (s, 1H), 8.11 (d, J=1.5 Hz, 1H), 8.03 (d, J=8.0 Hz, 2H), 7.89 (d, J=8.5 Hz, 2H), 7.85 (s, 1H), 7.42 (s, 1H). LC-MS calcd. for C$_{15}$H$_{10}$F$_3$N$_2$O$_2$ [(M+H)$^+$] 307, obsd. 306.8.

A mixture of 1-oxo-3-(4-trifluoromethyl-phenyl)-1,2-dihydro-pyrrolo[1,2-a]pyrazine-6-carbaldehyde (0.02 g, 65.3 µmol) in ethanol (0.25 mL) and tetrahydrofuran (0.25 mL) cooled to 0° C. was treated with sodium borohydride (3 mg, 79.3 µmol). The reaction was stirred at 0° C. for 1 h and then was stored in the refrigerator overnight. At this time, the reaction was concentrated in vacuo. The remaining solid was triturated with water, collected by filtration, washed with water and dried in vacuo to afford 6-hydroxymethyl-3-(4-trifluoromethyl-phenyl)-2H-pyrrolo[1,2-a]pyrazin-1-one (10 mg, 50%) as an off-white solid. $^1$H NMR (DMSO-d$_6$) δ ppm 7.87-7.96 (m, 3H), 7.79-7.87 (m, 2H), 7.40 (s, 1H), 6.87 (s, 1H), 5.03 (t, J=5.4 Hz, 1H), 4.50 (d, J=5.0 Hz, 2H). LC-MS calcd. for C$_{15}$H$_{12}$F$_3$N$_2$O$_2$ [(M+H)$^+$] 309, obsd. 309.0.

EXAMPLE 9

3-[4-(2-Fluoro-phenyl)-piperazin-1-yl]-6-methyl-2H-pyrrolo[1,2-a]pyrazin-1-one

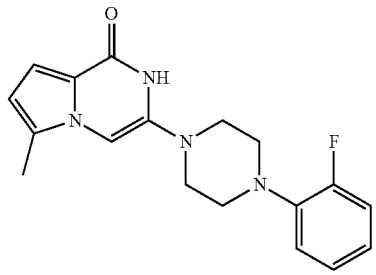 [SMILES: Cc1ccc2c(=O)[nH]c(N3CCN(c4ccccc4F)CC3)cn12]

A solution of ethyl 5-methyl-1H-pyrrole-2-carboxylate (1 g, 6.53 mmol) in anhydrous N,N-dimethylformamide (20 mL) under nitrogen at 0° C. was treated with a 60% dispersion of sodium hydride in mineral oil (392 mg, 9.79 mmol). After effervescence ceased, the reaction was treated with a solution of 2-bromoacetonitrile (1.17 g, 9.79 mmol) in N,N-dimethylformamide (2 mL). The resulting mixture was allowed to warm to room temperature and was stirred at room temperature for 30 min. At this time, the reaction was diluted with ethyl acetate (200 mL), washed with water (2×100 mL) and a saturated aqueous sodium chloride solution (2×100 mL), dried over sodium sulfate, filtered and concentrated in vacuo. Flash chromatography (80 g silica gel column, 0-20% ethyl acetate/hexanes) afforded ethyl 1-(cyanomethyl)-5-methyl-1H-pyrrole-2-carboxylate (0.5 g, 39.8%). LC-MS calcd. for C$_{10}$H$_{13}$N$_2$O$_2$ [(M+H$^+$] 193, obsd. 193.1.

A high pressure reaction vessel charged with ethyl 1-(cyanomethyl)-5-methyl-1H-pyrrole-2-carboxylate (848 mg, 4.41 mmol) cooled to 0° C. was treated with a 2M solution of hydrochloric acid in diethyl ether (30 mL, 60 mmol) and absolute ethanol (406 mg, 8.82 mmol). The mixture was stirred at 0° C. for 10 min and then was warmed to room temperature where it stirred over the weekend. At this time, the mixture was diluted with hexanes. The resulting precipitate was collected by filtration to afford ethyl 1-(2-ethoxy-2-iminoethyl)-5-methyl-1H-pyrrole-2-carboxylate hydrochloride (1.16 g, 95.7%) as a white solid. LC-MS calcd. for C$_{12}$H$_{19}$N$_2$O$_3$ [(M+H)$^+$] 239, obsd. 239.0.

A mixture of ethyl 1-(2-ethoxy-2-iminoethyl)-5-methyl-1H-pyrrole-2-carboxylate hydrochloride (950 mg, 3.46 mmol) and 1-(2-fluorophenyl)piperazine (1.87 g, 10.4 mmol) in ethanol (5 mL) was heated at 55° C. overnight. At this time, the reaction was concentrated in vacuo. Reverse phase column chromatography (0-100% acetonitrile/water) afforded ethyl 1-(2-(4-(2-fluorophenyl)piperazin-1-yl)-2-iminoethyl)-5-methyl-1H-pyrrole-2-carboxylate (1.1 g, 85.4%) as a white solid. LC-MS calcd. for C$_{20}$H$_{26}$N$_4$O$_2$ [(M+H)$^+$] 373, obsd. 373.0.

A mixture of ethyl 1-(2-(4-(2-fluorophenyl)piperazin-1-yl)-2-iminoethyl)-5-methyl-1H-pyrrole-2-carboxylate (150 mg, 0.4 mmol) and N,N-diisopropylethylamine (1.41 mL, 8 mmol) in tetrahydrofuran (4 mL) was heated at 150° C. in a microwave reactor for 3 h. At this time, the solution was cooled to room temperature. The resulting precipitate was collected by filtration, washed with minimal ethyl acetate and air dried to afford 3-[4-(2-fluoro-phenyl)-piperazin-1-yl]-6-methyl-2H-pyrrolo[1,2-a]pyrazin-1-one (115 mg, 87.5%) as a white solid. $^1$H NMR (300 MHz, DMSO-d$_6$) δ ppm 10.55 (s, 1H), 7.21-7.06 (m, 3H), 7.05-6.96 (m, 1H), 6.73 (d, 1H), 6.53 (s, 1H), 6.26 (d, 1H), 3.15 (s, 8H), 2.26 (s, 3H). LC-MS calcd. for $C_{18}H_{20}FN_4O$ $[(M+H)^+]$ 327, obsd. 326.9.

EXAMPLE 10

6-Bromo-3-(4-trifluoromethyl-phenyl)-2H-pyrrolo[1,2-a]pyrazin-1-one

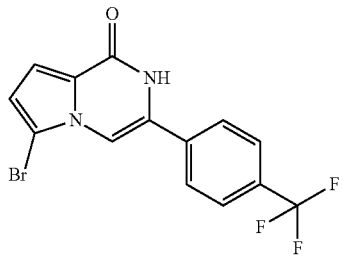

A solution of 2-bromo-1-(4-(trifluoromethyl)phenyl)ethanone (160 mg, 0.59 mmol), 2-bromo-1-(4-(trifluoromethyl)phenyl)ethanone (160 mg, 0.59 mmol,) and potassium carbonate (100 mg, 0.72 mmol,) in N,N-dimethylformamide (3 mL) was stirred at room temperature overnight. The reaction mixture was quenched with water and was extracted with diethyl ether. The organic layers were combined, dried over sodium sulfate, filtered and concentrated in vacuo. The remaining brown oil was purified by flash chromatography (12 g column, 0-15%) ethyl acetate/hexanes) to afford 5-bromo-1-[2-oxo-2-(4-trifluoromethyl-phenyl)-ethyl]-1H-pyrrole-2-carboxylic acid methyl ester (125 mg, 64%) as light yellow solid. $^1$H NMR (chloroform-d) δ ppm 8.13 (d, J=8.0 Hz, 2H), 7.82 (d, J=8.3 Hz, 2H), 7.05 (d, J=1.8 Hz, 1H), 6.87 (d, J=1.8 Hz, 1H), 5.73 (s, 2H), 3.75 (s, 3H).

A mixture of 5-bromo-1-[2-oxo-2-(4-trifluoromethyl-phenyl)-ethyl]-1H-pyrrole-2-carboxylic acid methyl ester (0.09 g, 0.23 mmol) and ammonium acetate (90 mg, 1.17 mmol) in glacial acetic acid (3 mL) were heated to 130° C. overnight. At this time, the reaction was treated with water. The resulting precipitate was collected by filtration, washed with water and dried in vacuo to afford 6-bromo-3-(4-trifluoromethyl-phenyl)-2H-pyrrolo[1,2-a]pyrazin-1-one (80 mg, 97%) as light brown solid. $^1$H NMR (chloroform-d) δ ppm 7.75-7.83 (m, 7H), 7.68-7.74 (m, 2H), 7.27 (d, J=1.5 Hz, 1H), 7.23 (s, 1H), 7.20 (s, 1H). LC-MS calcd. for $C_{14}H_7BrF_3N_2O$ $[(M-H)^-]$ 356, obsd. 354.9.

EXAMPLE 11

μHTS-TNKS-IWR2 TR-FRET Binding Assay (10 μL/well in BD1536-well plate, a single point)

Reagents and Stock Solutions

Tankyrase 1 (TNKS1): 184.3 μM=5.2 mg/mL His6-TNKS1, MW=28.2 KDa (construct: 1088-1327, I266M) in 20 mM Tris pH 8, 150 mM NaCl, 10% glycerol, and 0.5 mM TCEP Alternatively, in place of His6-TNKS1 can use either His6-tankyrase 2 (construct: 934-1166) (His6-TNKS2) or His6-PARP1 (full length).

Biotin-IWR2: 10 mM Biotin-IWR2 stock in DMSO, stored at −20° C.

Positive control: 10 mM XAV 939 in DMSO, stored at −20° C.

Eu-Streptavidin: 38.1 μM (2.1 mg/mL) Eu-SA (Bio #Eu-2212, Lot #N 18001-BDHO2)

APC-anti-His Ab: 8.50 μM SL-APC, 8.26 μM anti-6His antibody-SureLight APC (Columia Bioscience, Cat #D3-1711, Lot #N01010-AAH04)

Assay plate: BD 1536-well, clear/black plate (Cat #353255)

NP-40: 10% NP-40 solution (PIERCE, Cat #28324, Lot #97101671)

Assay Buffer Preparation

Assay buffer 1a (AB1a) for TNKS dilution: 50 mM Tris, pH 7.4, 100 mM sodium chloride solution, 1 mM magnesium chloride solution, 1 mM DL-dithiothreitol solution, 0.2 mg/mL bovine serum albumin solution, 0.025% NP-40.

Assay buffer 1b (AB1b) for Biotin-IWR2 dilution: 50 mM Tris, pH 7.4, 100 mM sodium chloride solution, 1 mM magnesium chloride solution, 1 mM DL-dithiothreitol solution, 0.2 mg/mL bovine serum albumin solution, 0.05% NP-40

Assay buffer 1c (AB1c) for compound dilution: 50 mM Tris, pH 7.4, 100 mM sodium chloride solution, 1 mM magnesium chloride solution, 1 mM DL-dithiothreitol solution, 0.2 mg/mL bovine serum albumin solution Assay buffer 2 (AB2) for Eu/APC: 50 mM Tris, pH 7.4, 100 mM sodium chloride solution, 1 mM magnesium chloride solution, 0.2 mg/mL bovine serum albumin solution Prepare Biotinylated IWR2 stock solution (3.33× stock) for TOTL and cpd wells: 200 nM Biotin-IWR2 in 5% DMSO/AB1b buffer Prepare BLANK well stock solution: 5% DMSO/AB1b buffer Prepare POSITIVE CONTROL well stock solution (3.33× stock): 200 nM XAV939 in 200 nM Biotin-IWR2/5% DMSO/AB1b buffer Prepare TNKS1 stock solution (5× stock): 300 nM TNKS in AB1a buffer (Alternatively, use TNKS2 or PARP1 stock solutions.)

Prepare Eu/APC stock solution (5× stock): 3.5 nM Eu-SA/50 nM APC-His6Ab in AB2 buffer

Assay Procedure

Compound Preparations:

Add 25 μL/well 1.5% DMSO/AB1c buffer in each compound well to the compound concentration at 74 μM in 8.8% DMSO/AB1c buffer or in the 2 μL DMSO CONTROL wells (BLANK, TOTAL and POSITIVE wells) in the compound plate.

Transfer 3 μL/well of above solution (solution 1, 2, 3) to an empty assay plate (BD1536-well plate) as follows:

TOTAL and cpd wells: Solution 1 (Biotin-IWR2):
BLANK wells: Solution 2 (No Biotin-IWR2):
POSITIVE CONTROL wells: Solution 3 (Biotin-IWR2+XAV939)

Transfer 3 μL/well of the above diluted compound solutions or compound dilution buffer to the above assay plate.

Add 2 μL/well of 300 nM TNKS stock solution (4) to every well in the above assay plate Centrifuge the assay plate at 2100 rpm for 2 minutes.
Incubate the assay plate at 26° C. for 30 minutes.
Add 2 μL/well 3.5 nMEu/50 nM APC solution (5) to every well in the above assay plate.
Centrifuge the assay plate at 2100 rpm for 2 minutes.
Incubate the assay plate at 26° C. for 60 minutes.

Read the assay plate immediately at excitation wavelength of 330 nM and emission wavelength of 615 and 665 nM in time resolved fluorescence mode.

Final Assay Conditions

Biotin-IWR2: 60 nM

TNKS: 60 nM

Eu-SA: 0.7 nM

APC-His Ab: 10 nM

XAV939 (+ve control): 60 nM at ~70% Inhibition

General Library compounds: 22.23 μM in 4% DMSO

Representative compound data for assays are listed below in Table I.

TABLE 1

| Example | TNKS1 IC$_{50}$ (μM) | TNKS2 IC$_{50}$ (μM) | PARP1 IC$_{50}$ (μM) |
|---|---|---|---|
| 1 | 0.054 | 0.145 | >50 |
| 2 | 0.232 | 0.995 | 31.19 |
| 3 | 0.192 | 1.261 | >50 |
| 4 | 0.770 | 1.901 | 29.48 |
| 5 | 6.789 | 12.73 | >50 |
| 6 | 1.113 | 1.839 | 34.89 |
| 7 | 0.032 | 0.072 | 0.1715 |
| 8 | 0.0170 | 0.715 | 11.4 |
| 9 | 0.068 | 0.068 | 2.744 |
| 10 | 0.056 | 0.158 | 1.25 |

EXAMPLE 12

Pharmaceutical compositions of the subject Compounds for administration via several routes can be prepared as described in this Example.

Composition for Oral Administration (A)

| Ingredient | % wt./wt. |
|---|---|
| Active ingredient | 20.0% |
| Lactose | 79.5% |
| Magnesium stearate | 0.5% |

The ingredients are mixed and dispensed into capsules containing about 100 mg each; one capsule would approximate a total daily dosage.

Composition for Oral Administration (B)

| Ingredient | % wt./wt. |
|---|---|
| Active ingredient | 20.0% |
| Magnesium stearate | 0.5% |
| Crosscarmellose sodium | 2.0% |
| Lactose | 76.5% |
| PVP (polyvinylpyrrolidine) | 1.0% |

The ingredients are combined and granulated using a solvent such as methanol. The formulation is then dried and formed into tablets (containing about 20 mg of active compound) with an appropriate tablet machine.

Composition for Oral Administration (C)

| Ingredient | % wt./wt. |
|---|---|
| Active compound | 1.0 g |
| Fumaric acid | 0.5 g |
| Sodium chloride | 2.0 g |
| Methyl paraben | 0.15 g |
| Propyl paraben | 0.05 g |
| Granulated sugar | 25.5 g |
| Sorbitol (70% solution) | 12.85 g |
| Veegum K (Vanderbilt Co.) | 1.0 g |
| Flavoring | 0.035 ml |
| Colorings | 0.5 mg |
| Distilled water | q.s. to 100 ml |

The ingredients are mixed to form a suspension for oral administration.

Parenteral Formulation (D)

| Ingredient | % wt./wt. |
|---|---|
| Active ingredient | 0.25 g |
| Sodium Chloride | qs to make isotonic |
| Water for injection to | 100 ml |

The active ingredient is dissolved in a portion of the water for injection. A sufficient quantity of sodium chloride is then added with stirring to make the solution isotonic. The solution is made up to weight with the remainder of the water for injection, filtered through a 0.2 micron membrane filter and packaged under sterile conditions.

Suppository Formulation (E)

| Ingredient | % wt./wt. |
|---|---|
| Active ingredient | 1.0% |
| Polyethylene glycol 1000 | 74.5% |
| Polyethylene glycol 4000 | 24.5% |

The ingredients are melted together and mixed on a steam bath, and poured into molds containing 2.5 g total weight.

Topical Formulation (F)

| Ingredients | grams |
|---|---|
| Active compound | 0.2-2 |
| Span 60 | 2 |
| Tween 60 | 2 |
| Mineral oil | 5 |
| Petrolatum | 10 |
| Methyl paraben | 0.15 |
| Propyl paraben | 0.05 |
| BHA (butylated hydroxy anisole) | 0.01 |
| Water | q.s. 100 |

All of the ingredients, except water, are combined and heated to about 60° C. with stirring. A sufficient quantity of water at about 60° C. is then added with vigorous stirring to emulsify the ingredients, and water then added q.s. about 100 g.

The features disclosed in the foregoing description, or the following claims, expressed in their specific forms or in terms of a means for performing the disclosed function, or a method or process for attaining the disclosed result, as appropriate, may, separately, or in any combination of such features, be utilized for realizing the invention in diverse forms thereof.

The foregoing invention has been described in some detail by way of illustration and example, for purposes of clarity and understanding. It will be obvious to one of skill in the art that changes and modifications may be practiced within the scope of the appended claims. Therefore, it is to be understood that the above description is intended to be illustrative and not restrictive. The scope of the invention should, therefore, be determined not with reference to the above description, but should instead be determined with reference to the following appended claims, along with the full scope of equivalents to which such claims are entitled.

The patents, published applications, and scientific literature referred to herein establish the knowledge of those skilled in the art and are hereby incorporated by reference in their entirety to the same extent as if each was specifically and individually indicated to be incorporated by reference. Any conflict between any reference cited herein and the specific teachings of this specifications shall be resolved in favor of the latter. Likewise, any conflict between an art-understood definition of a word or phrase and a definition of the word or phrase as specifically taught in this specification shall be resolved in favor of the latter.

We claim:

1. A compound of the formula (I): wherein

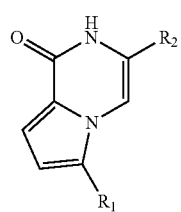

(I)

$R_1$ is selected from the group consisting of $C_{1-6}$ alkyl, halo, cyano, $C_{1-6}$ hydroxyalkyl,

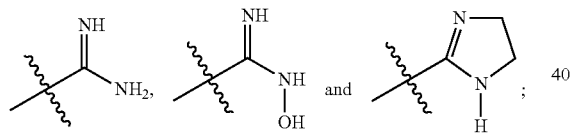

and $R_2$ is aryl, pyridinyl, piperazinyl or piperidinyl, where said aryl or pyridinyl is optionally substituted by one or three groups independently selected from $C_{1-6}$ alkyl, $C_{1-6}$ alkoxy, $C_{1-6}$ haloalkyl or halogen and where said piperazinyl or piperidinyl is optionally substituted by aryl wherein said aryl is further optionally substituted by one or three groups independently selected from $C_{1-6}$ alkyl, $C_{1-6}$ alkoxy, $C_{1-6}$ haloalkyl or halogen; or, a pharmaceutically acceptable salt thereof.

2. The compound of claim 1 wherein $R_2$ is

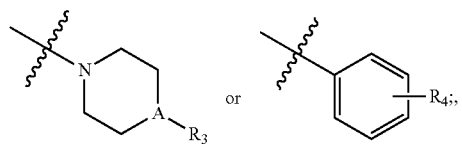

A is CH or N;
$R_3$ is optionally substituted aryl; and,
$R_4$ is trifluoromethyl or methoxy.

3. The compound of claim 1 wherein $R_2$ is optionally substituted pyridinyl.

4. The compound of claim 1 selected from the group consisting of
6-Bromo-3-(4-methoxy-phenyl)-2H-pyrrolo[1,2-a]pyrazin-1-one,
1-Oxo-3-(4-trifluoromethyl-phenyl)-1,2-dihydro-pyrrolo[1,2-a]pyrazine-6-carbonitrile,
N-Hydroxy-1-oxo-3-(4-trifluoromethyl-phenyl)-1,2-dihydro-pyrrolo[1,2-a]pyrazine-6-carboxamidine,
1-Oxo-3-(4-trifluoromethyl-phenyl)-1,2-dihydro-pyrrolo[1,2-a]pyrazine-6-carboxamidine,
6-(4,5-Dihydro-1H-imidazol-2-yl)-3-(4-trifluoromethyl-phenyl)-2H-pyrrolo[1,2-a]pyrazin-1-one,
6-Methyl-3-(4-trifluoromethyl-phenyl)-2H-pyrrolo[1,2-a]pyrazin-1-one,
6-Hydroxymethyl-3-(4-trifluoromethyl-phenyl)-2H-pyrrolo[1,2-a]pyrazin-1-one,
3-[4-(2-Fluoro-phenyl)-piperazin-1-yl]-6-methyl-2H-pyrrolo[1,2-a]pyrazin-1-one, and
6-Bromo-3-(4-trifluoromethyl-phenyl)-2H-pyrrolo[1,2-a]pyrazin-1-one.

5. A pharmaceutical composition comprising a compound according to claim 1 and a pharmaceutically acceptable carrier.

6. A compound of the formula (I): wherein

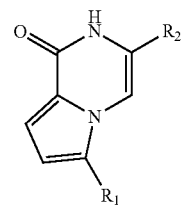

(I)

$R_1$ is

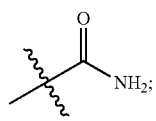 [SMILES: *C(N)=O]

and $R_2$ is aryl,
pyridinyl, piperazinyl or piperidinyl, where said aryl or pyridinyl is optionally substituted by one or three groups independently selected from $C_{1-6}$ alkyl, $C_{1-6}$ alkoxy, $C_{1-6}$ haloalkyl or halogen and where said piperazinyl or piperidinyl is optionally substituted by aryl wherein said aryl is further optionally substituted by one or three groups independently selected from $C_{1-6}$ alkyl, $C_{1-6}$ alkoxy, $C_{1-6}$ haloalkyl or halogen; or,
a pharmaceutically acceptable salt thereof.

7. The compound of claim 6 which is 1-oxo-3-(4-trifluoromethyl-phenyl)-1,2-dihydro-pyrrolo[1,2-a]pyrazine-6-carboxylic acid amide.

* * * * *